United States Patent [19]

Hardy et al.

[11] 4,333,735
[45] Jun. 8, 1982

[54] PROCESS AND APPARATUS FOR MEASURING GASEOUS FIXED NITROGEN SPECIES

[75] Inventors: James E. Hardy, Scotch Plains; John J. Knarr, South Plainfield, both of N.J.

[73] Assignee: Exxon Research & Engineering Co., Florham Park, N.J.

[21] Appl. No.: 244,205

[22] Filed: Mar. 16, 1981

[51] Int. Cl.³ .................. G01N 21/75; G01N 31/12
[52] U.S. Cl. .................. 23/232 R; 23/230 PC; 23/232 E; 422/52; 422/78; 422/91
[58] Field of Search .......... 23/232 R, 232 E, 230 PC; 422/78, 52, 80, 83, 91

[56] References Cited
U.S. PATENT DOCUMENTS 3,647,387  3/1972  Benson et al.
3,919,397  11/1975 Gould
3,996,008  12/1976 Fine et al. ..................... 422/52
4,070,155  1/1978  Fraim ....................... 23/230 PC

FOREIGN PATENT DOCUMENTS 2851821  5/1979  Fed. Rep. of Germany

OTHER PUBLICATIONS

EPRI Report No. 223-1 (Mar. 1976) by R. F. Sawyer et al.
ACS Abstract, 173rd ACS Nat'l Meeting, New Orleans, Mar. 20-25, 1977, Environ Chem. Prepr. 17 #1:11-12.
NTIS Publication PB 298248 (Feb., 1974) "Optimized Chemiluminescence System for Measuring Atmospheric Ammonia".

Primary Examiner—Arnold Turk
Attorney, Agent, or Firm—Robert J. North

[57] ABSTRACT

Process and apparatus for measuring total fixed gaseous nitrogen species, including $NH_3$, $NO$, $NO_2$, $HCN$ and organic amines in gaseous mixtures. The process involves catalytic conversion at elevated temperature of all fixed nitrogen species to nitric oxide, $NO$, followed by chemiluminescent measurement of the resulting $NO$ concentration. The improvement features of the process are the use of a reduced pressure gaseous sample flow to prevent $N_2$ poisoning of the heated platinum catalyst and a preheat step of the reduced pressure gaseous mixture in an inert, non-catalytic quartz preheater prior to catalytic conversion to prevent loss of some species, such as $NH_3$, through premature catalyzed reaction with $NO$ and subsequent loss from the system as $N_2$.

20 Claims, 4 Drawing Figures

CONVERSION EFFICIENCY AS A FUNCTION OF TEMPERATURE FOR PLATINUM-BASED CONVERTER.

(○) Low-pressure (10 kPaA); 740ppm $NH_3$; 4% $O_2$, balance He
(□) Low-pressure (10 kPaA); 400ppm HCN, 4% $O_2$, balance He
(△) Atmospheric pressure; 600ppm $NH_3$, 2% $O_2$, balance He MEASURED $NO_x$ AS A FUNCTION OF INPUT $NH_3$ AND HCN Conditions: Converter temperature = 1030K; 4% $O_2$, (□)150-2500ppm $NH_3$ determined by HCl titration; (o) 50-2300ppm HCN determined by argentimetry, balance nitrogen.

PROCESS AND APPARATUS FOR MEASURING GASEOUS FIXED NITROGEN SPECIES

BACKGROUND OF THE INVENTION

1. Field of the Invention

This invention relates to an improved process and apparatus for measuring total fixed nitrogen species in a gaseous mixture by catalytically converting all of the species to NO and measuring the resulting NO concentration by chemiluminescence. More particularly, the improvements include reducing the pressure of the gaseous mixture followed by preheating in an inert non-catalytic preheater prior to catalytic conversion to NO.

2. Brief Description of the Prior Art

An integral part of combustion research and $NO_x$ emission studies is the measurement of total fixed nitrogen species in gaseous effluents, such as automotive exhausts. Generally, the goal is to measure the concentration of combustion product nitrogen oxides ($NO_x$) including $NO_2$ and NO, which are considered to be toxic in the environment. These data can then be correlated with variables in the combustion process, for example to devise ways for reducing the amounts of these species in the exhaust effluents.

Methods are known in the art for the conversion of these nitrogen oxides under thermal and catalytic conditions to form primarily NO, and then measuring the resulting NO concentration by the technique of NO chemiluminescence.

U.S. Pat. No. 3,647,387, for example, describes the chemiluminescent detection of NO produced from pyrolyzing nitrogen compounds by contacting gaseous nitrogen species at 1000°–1250° K. with a copper or platinum catalyst.

Similarly, U.S. Pat. No. 3,919,397 describes the preparation of a gaseous mixture containing $NO_2$ and NO for chemiluminescent measurement by first passing the mixture through a series of parallel alumina tubes containing a resistivity heated platinum wire to convert all of the $NO_2$ to NO.

Not only are nitrogen oxides of interest in combustion research, but also is the concentration of $NH_3$, and HCN, species which are also present in combustion effluents and especially from fuel-rich mixtures.

EPM Report No. 223-1 (March 1976) describes the efficiency of various catalysts in the conversion of various species to NO for chemiluminescent analysis. Platinum is described as being an effective catalyst for converting $NH_3$ to NO and also described is the enhancement of this conversion at lower pressures and the associated catalytic effect of stainless steel equipment.

It is, however, generally recognized in the field that there is no rapid, accurate and reproducible technique for the measurement of $NH_3$ or HCN in combustion effluents, especially in rich combustion gases. Further, we have found that currently available commercial instruments, which use stainless steel as the $NO_x$ converter housing are not satisfactory for measuring $NH_3$ or HCN concentration, particularly when using nitrogen as the diluent gas.

SUMMARY OF THE INVENTION

We have unexpectedly discovered a process, and an apparatus for carrying out the process, for the rapid and accurate determination of total fixed nitrogen species in gaseous mixtures which accurately includes the contribution of $NH_3$ and HCN, as well as other fixed nitrogen species in the total determination.

It has been discovered that gaseous nitrogen adversely affects the efficiency of a precious metal catalyst, particularly platinum, in a catalytic converter at elevated temperatures and it has been further discovered that by carrying out the catalytic conversion at reduced pressures, in the order of 0.03 MPa and below, that the platinum catalyst in the system remains relatively stable over long periods of time.

In addition, it has been discovered that the accuracy and reproducibility of the process can be improved if the gaseous mixture is preheated under inert conditions in an initial step prior to conversion to NO in the catalytic converter, wherein the reaction $NH_3 + O_2 \rightarrow NO$, proceeds at 800°–1100° K. in reference to any competing reactions. The preheat step is conducted at about 700°–1100° K. and preferably in a quartz tube such that no wall catalytic effects are present. It is believed that the undesirable reaction:

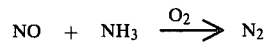

$$NO + NH_3 \xrightarrow{O_2} N_2$$

can occur catalytically in the temperature region of 500°–1100° K. whereas the same reaction thermally induced is believed not to occur until higher temperatures than 1100° K. are achieved. If the catalytic effect occurs, then the conversion efficiency for $NH_3$ to NO is lowered and erratic values for the total value of gaseous fixed nitrogen species are obtained. In addition, the preheat step insures that the required temperature of the gaseous nitrogen species for catalytic conversion to NO is obtained which increases the speed and efficiency of the process.

By the invention there is provided an improved process for measuring the total concentration of fixed nitrogen species, including NO, $NO_2$, $NH_3$ and HCN, in a gaseous mixture involving the steps of contacting said gaseous mixture with a conversion catalyst at elevated temperature and in the presence of excess elemental oxygen and thereby converting said fixed nitrogen species to NO and measuring the resulting NO concentration and calculating therefrom said total concentration of gaseous fixed nitrogen species, in which the improvement comprises the combined steps of:

(a) reducing the pressure of said gaseous stream to about 0.03 MPa or below;

(b) preheating said gaseous mixture from step (a) to a temperature in the range of about 700°–1100° K. in a non-catalytic preheat zone; and (c) contacting said preheated gaseous mixture from step (b) with said conversion catalyst at a temperature in the range of about 800°–1100° K., for a sufficient time to convert substantially all of said fixed gaseous nitrogen species to NO.

Further, there is provided an improved apparatus for measuring the total concentration of fixed nitrogen species in a gaseous mixture, including NO, $NO_2$, $NH_3$ and HCN, involving a means for introducing said gaseous mixture into said apparatus, a catalytic converter for converting said fixed nitrogen species in said gaseous mixture at elevated temperature to NO and an NO detector for measuring the resulting NO concentration, in which the improvement comprises the combined elements of:

(a) means for reducing the pressure of said introduced gaseous mixture to about 0.03 MPa and below;

(b) a non-catalytic preheater for preheating said reduced pressure gaseous mixture in the temperature range of about 700°–1100° K., prior to contacting said catalytic converter.

Indicated $NO_x = (1.00 \pm 0.02) \times NH_3$, and
Indicated $NO_x = (1.01 \pm 0.03) \times HCN$.

DESCRIPTION OF THE INVENTION AND PREFERRED EMBODIMENTS

The process and apparatus of the instant invention are designed to achieve unit efficiency of conversion of total fixed nitrogen species in gaseous mixtures. By the improvement of utilizing reduced pressure gas flow, and a preheat step in the absence of catalytic effects, measurement of the total fixed gaseous species, including $NH_3$ and HCN, is insured.

By the term "gaseous mixture", as used herein, is meant a wide variety of gaseous environments including combustion effluents, such as automotive, boiler or furnace exhausts, gaseous mixtures in the vicinity of nitrogen oxide leaks and the like.

The term "total gaseous fixed nitrogen species" as used herein, and currently in the state of the art, does not include $N_2$ or $N_2O$, since these species are very stable and are only difficultly converted to NO for measurement. The forcing conditions necessary would interfere and actually obscure the presence of other species desired to be measured. However, the term does include NO, $NO_2$, $N_2O_4$, $NH_3$, HCN, organic amines such as methylamine, ethylamine, pyridine, and the like, and nitrites, nitrates, cyano compounds, amides, and the like.

The advantage of the subject process, as compared to prior art methods, is that it is more rapid, accurate, sensitive, and that since it is a total method by nature, it eliminates the possibility that some fixed nitrogen species will have been overlooked and left unmeasured. An advantage of the subject improved apparatus is that existing commercial apparati can easily be modified to incorporate the feature of the subject apparatus for carrying out the subject process.

Figure 1:
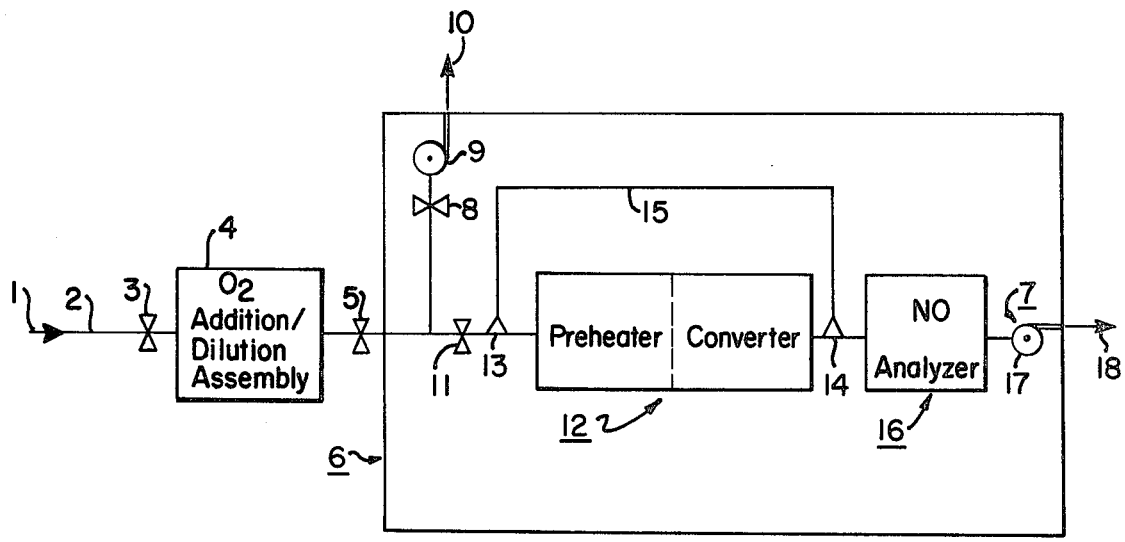
FIG. 1 is a schematic diagram of a preferred embodiment of the subject apparatus illustrating inlet means for the gaseous sample, pressure reducing means, catalytic converter assembly and chemiluminescent NO analyzer.
Figure 2:
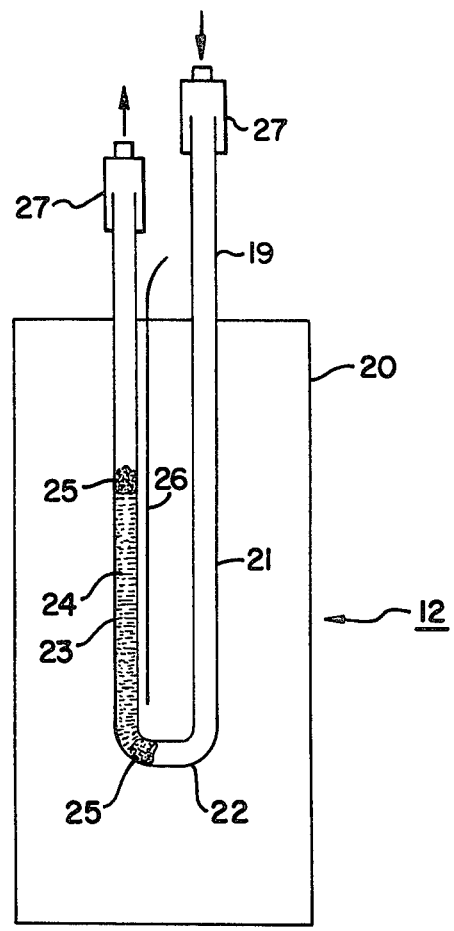
FIG. 2 is a diagram of a preferred embodiment; the improved preheater/catalytic converter assembly being a quartz U-tube which can conveniently be directly fitted into commercial chemiluminescent NO analyzer.

A clearer understanding of the process and apparatus can be achieved by referring to FIG. 1 which is a schematic diagram of a preferred embodiment of the subject improved apparatus. A gaseous sample 1 is introduced into the apparatus via gas inlet means 2 and flowmeter/controller assembly 3. The gaseous sample 1 is diluted and oxygen is added in the oxygen addition/diluting assembly 4 prior to admission to the converter/NO analyzer assembly 6. The gaseous sample 1 is of reduced, ambient or super-atmospheric pressure but when introduced, is reduced to a pressure of about 0.03 MPa or lower which is maintained by the action of pressure reducing means 7 comprising vacuum pump 17 and flow controllers 5, 8 and 11. The gaseous sample, now mixed with excess oxygen, is allowed to flow through flow controller valve 5 for passage to the converter/analyzer assembly 6. Excess sample is vented to the atmosphere at 10 by the bellows pump 9. The gaseous sample is allowed to pass through improved catalytic converter assembly 12, containing preheater and converter, where catalytic conversion of the total fixed gaseous nitrogen species, excluding $N_2$ and $N_2O$, to NO will occur substantially at unit efficiency. A schematic cross-section of a preferred embodiment of the converter assembly 12 is illustrated in FIG. 2 showing a preferred construction of the unit situated in heating/housing means 20. The catalytic converter assembly is comprised of a quartz tube 19 having a U-bend 22 separating preheat zone 21 (preheater) and catalytic zone 23 (catalytic converter). Tube fittings 27 are provided for insertion into the line assembly of standard commercial units. Thermocouple 26 measures the external temperature outside the catalytic zone 23 and preheat zone 21. The catalytic zone 23 comprises preferably 50 mesh platinum gauze as catalyst 24 packed tightly and sandwiched between two quartz wool plugs 25. The diluted, gaseous sample containing excess oxygen flows into preheat zone 21 of the quartz tube which is maintained at a temperature of about 700°–1100° K. The walls of the quartz tube in the preheat zone are scrupulously clean and free from dust, metallic deposition and the like which would tend to catalyze the reaction between NO and any of the fixed gaseous species, and particularly $NH_3$. After passing through the preheat zone, the sample is forced upward through the heated platinum gauze 24 wherein conversion of fixed nitrogen species to NO occurs. After conversion, the sample is allowed to pass to a conventional chemiluminescent NO analyzer 16, where the concentration of NO is determined through chemiluminescent reaction with ozone by means of an optical filter assembly and photomultiplier assembly (both not shown). The pressure in the catalytic converter is maintained by vacuum pump 17. The exiting gaseous mixture 18 is then vented. The system can be calibrated very exactly by means of introducing a standard concentration of NO in an inert diluent gas bypassing the internal catalytic converter 12 by means of bypass 15 and bypass valves 13 and 14, and passing the mixture into the chemiluminescent NO analyzer 16 for direct calibration purposes.

A preferred embodiment of the improved apparatus comprises the improved preheater/catalytic converter 12 as shown in FIG. 2 containing quartz tube 19 with noncatalytic preheat zone and catalytic conversion zone 23. The terms "preheater" and "preheat zone" are equivalent, as are "catalytic converter" and "catalyst zone" and respectively used interchangeably herein. The preheat zone has to exhibit high temperature stability and be constructed of a material which is "noncatalytic", i.e., which will inhibit catalytic wall effects from occurring to catalyze the reactions:

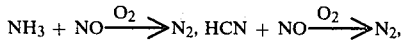

or reactions with other fixed nitrogen species. Included in the class of materials which will satisfy these criteria plus exhibit temperature stability in the region of 700°–1100° K., the necessary preheat temperature range, are chemically inert quartz, fused quartz, high purity alumina, and mullite. Preferred material for construction of the preheat zone is fused quartz, which can be obtained commercially.

As illustrated in FIG. 2, the quartz tube is preferably in the shape of a U-tube, housing both the preheat zone and catalytic converter, i.e., the platinum gauze catalyst, in one assembly. However, this is not mandatory, since the catalytic converter could be housed in a separate unit following the preheat zone, such as housed in a stainless steel assembly or the like. Preferably, however, it is convenient to employ the preheat zone and catalytic converter in one assembly. Further, the quartz tube housing is not required to be a U-tube but could also be a straight tube or other configuration in the assembly. Spaced considerations in commercial apparatus, however, render it preferable that the assembly be in the form of a U-tube. The size of the quartz tube may be any convenient conventional size. For example, the quartz tube illustrated in FIG. 2, is modelled after that which was actually used in the following Examples, and is 6.3 mm o.d., 200 mm in height and 2.5 ml in volume.

Length of the preheat section should be such that the sample gas is substantially preheated above a temperature of about 700° K. prior to contacting the converter zone. Length of the converter zone should be such that complete combustion of fixed nitrogen species to NO occurs. It is reasonably thought that proportionate scaleup of the apparatus as described, will result in substantially the same results when practicing the described process herein.

The means for reducing the pressure of the gas sample in the apparatus can be a vacuum pump, (such as element 17, as illustrated in FIG. 1) or conventional pressure-reducing pump for reducing the pressure of the gaseous sample down to about 0.03 MPa or lower.

The preheater or preheat zone is located in series prior to the catalytic converter and must be heated to about 700°–1100° K. which can be accomplished by any conventional type of heating means such as with a resistive wire wound around the quartz tube or heating element contained in the housing surrounding the quartz tube assembly. Also, the heat can be generated from the near proximity to the catalyst zone as illustrated in FIG. 2 which is maintained at a temperature of about 800°–1100° K., and preferably about 800°–1000° K., preferably, the temperature of the preheat zone and converter are substantially the same, being in the range of about 850°–1000° K.

The converter catalyst comprises platinum and can be in the form of a wire, powder, granular mesh and the like. Preferred is platinum metal in the form of gauze in sizes 1 to 200 mesh and preferably size 50 mesh. Other catalysts which can be used must be stable under the oxidation conditions, such as platinum nitric acid oxidation catalysts and include, for example, platinum/rhodium alloys. The platinum catalyst must, of course, be physically separated from the preheat zone to avoid providing catalytic particles or bases for the preheated gas. This can be readily accomplished by a variety of techniques and one convenient method is the use of quartz wool plugs as illustrated in the preferred embodiments herein.

Preferably, the catalytic converter and preheater are one assembly which is preferably a quartz vessel.

Other elements of the subject improved apparatus are adequately described in the Figures and following Examples and are conventional, such as the chemiluminescent NO analyzer, and need not be discussed further. Other embodiments incorporating the improved apparatus features of non-catalytic preheater, or non-catalytic preheater/converter assembly coupled with means for producing reduced pressure sample flow will be obvious to one skilled in the art from this disclosure.

The improved subject process involves the catalytic conversion of gaseous fixed nitrogen species in a non-catalytically preheated gaseous sample, at a pressure of about 0.03 MPa or below, preferably about 0.001–0.03 MPa, and particularly preferred about 0.005 MPa. The improvement preheat step is conducted at a temperature of about 700°–1100° K., preferably about 800°–1000° K. under inert, non-catalytic conditions, such that reaction between NO and other fixed nitrogen species is avoided, as described hereinabove.

The nature of the preheat zone and conversion catalyst have been adequately described above and need not be reiterated. Preferably, the preheat zone is constructed of fused quartz and the catalyst is 50 mesh platinum gauze.

The degree of conversion of the fixed nitrogen species obtained is essentially quantitative, i.e., unit efficiency. This can be obtained by contacting the gaseous preheated mixture for a sufficient time with the catalyst within the scope of reaction variables described herein, to insure complete conversion and this is readily obvious to one skilled in the art from this disclosure without an undue amount of experimentation.

By the term "measuring the resulting NO concentration" in the improved process herein, is meant any method which is suitable for carrying out that end. A preferred embodiment, as disclosed herein, is utilizing for this purpose, a chemiluminescent NO analyzer. However, other reliable techniques such as laser absorption, fluorescence spectroscopy, wet methods and the like, may also be used.

The calculation of the total fixed nitrogen species from the resulting NO concentration is conventional and known in the art.

Periodic rejuvenation of the platinum catalyst may be necessary and may be accomplished by contacting the used catalyst with a reducing gas such as ammonia or hydrogen in an inert carrier such as helium, at elevated temperature for a few minutes.

Flow rates of the gaseous mixture in the process can be operated conveniently from about 300 cc/min to 5000 cc/min. Preferably, a flow rate of about 1000 cc/min is used. However, slower and faster flow rates can also be used in the process.

The residence times of the gaseous mixture in the catalytic converter are in the order of about 10 to 10,000 milliseconds and preferably about 100 to 1000 milliseconds. However, higher and lower residence times can also be conveniently utilized.

The above values for flow rates and residence times are not critical nor limiting and are those obtained in the process when utilizing 50 mesh platinum gauze as conversion catalyst under the catalyst configurations, other values of flow rates and residence times may be more convenient. These will be obvious to one skilled in the art from this disclosure without an undue amount of experimentation.

Temperature of the gaseous mixture, as introduced into the apparatus, should be below about 250° C. to avoid reaction catalyzed by stainless steel tubing. If the gaseous mixture is higher in temperature than about 250° C., and the apparatus contains stainless steel fittings and/or tubing, it should be cooled by conventional means prior to introduction into the apparatus.

Other embodiments and modifications of the subject improved process and apparatus will become obvious to one skilled in the art from this disclosure.

The following examples illustrate the best mode of carrying out the subject invention as contemplated by us and should not be construed as being limitations on the scope and spirit of the instant invention.

EXPERIMENTAL

General Description of the Apparatus

The apparatus used was similar to the schematic diagram in FIG. 1 and consisted of a rotameter mixing manifold for preparing the inlet gaseous sample, an analytical system for measuring $O_2$ and NO, and an absorption train to permit the measurement of HCN and $NH_3$ by wet-chemical methods. The mixing manifold was a two-stage dilution-blending apparatus using rotameters for He or $N_2$, $O_2$, $CO_2$, $NH_3$, and HCN/He or NO/He. Research quality pure gases were obtained from several suppliers. The HCN/He mixture was obtained from Scientific Gas Products as an analyzed gas mixture. NO/He mixtures were obtained from Airco Industrial Gases as analyzed mixtures. The compositions of the gas mixtures prepared by dilution/blending were calculated using Fisher-Porter rotameter sizing procedures and confirmed by measurement on the analytical system.

The analytical system included a Teledyne Electrochemical $O_2$ analyzer with provision for calibrating it with laboratory air or $N_2$, and a Thermoelectron Model 10 A Chemiluminescent NO analyzer with an internal stainless steel catalytic converter supplied by the manufacturer. The chemiluminescent analyzer was calibrated using a 200 ppm NO/He standard from Matheson Gas Products. Other instruments in the analytical system were bypassed for these experiments. A Fairchild backpressure regulator at the end of the analysis line, immediately before the chemiluminescent NO analyzer, was used to maintain the sample pressure at +1 kPag while maintaining delay times of 10-30 seconds.

Special apparati were used in these experiments in conjunction with the conventional chemiluminescent NO analyzer. One was the oxygen addition/diluter assembly 4, which served to reduce the dew point of the gas to be analyzed. The second was the subject reactor shown in FIG. 2 which was operated at low pressure (~10 kPa) by connecting it in place of the conventional internal converter in the chemiluminescent NO analyzer using 3.15 mm o.d. Teflon tube connections.

The converter/preheater assembly was constructed of a fused quartz tube, commercially available from Thermal American Fused Quartz Company, under the tradename "Vitreosil", and was 6.3 mm o.d., 250 mm long and of 2.5 ml volume. The tube was bent into a U-shaped configuration using a hydrogen torch.

General Description of the Procedure

Gaseous mixtures, prepared by rotameter manifold blending, were introduced into gas inlet assembly, under a pressure of about 0.12 MPa and at ambient temperature. A Fairchild backpressure regulator was set to control sample pressure at 7 kPag. By means of a Matheson 8116 mass flowmeter, the sample was allowed to flow at 300 ml/min. prior to dilution. Dilution with air or $N_2$ was achieved by adding an amount of diluent gas by means of a Matheson 8240 mass flow controller. The resulting diluted gaseous sample could also be mixed with oxygen via an oxygen feed assembly resulting in a diluted gaseous sample containing about 0.1 to 20 vol. % $O_2$ prior to conversion. The diluted, $O_2$-containing gas was then introduced into the quartz preheat zone, maintained at a temperature of about 1000° K. and then into the catalytic converter, containing a column of about 1.5 grams of 50 mesh platinum gauze retained at each end by quartz wool plugs. The temperature of the converter zone was about 800°–1100° K., as measured by a K-type thermocouple. The sample exiting from the converter was fed into the chemiluminescent NO analyzer where NO concentration was determined.

CALIBRATION TECHNIQUES

Calibration of the apparatus was accomplished by determining the $NH_3$ and HCN concentrations of the gas mixtures by wet-chemical methods, and calibrating the chemiluminescent NO analyzer with a standard gas mixture. $NH_3$ was measured by HCl titration, this being a procedure with a precision of 5% and being directly traceable to an absolute standard. Likewise, HCN was measured by argentimetry. The accuracy of the NO analyzer was verified by standardization with an NBS-traceable $NO/N_2$ gas mixture obtained from Airco Industrial Gases.

EXAMPLE 1

Utilizing the apparatus described above, and a quartz-platinum catalytic converter, as illustrated in FIG. 2, the following series of runs were made and the results listed below in Table I.

For the atmospheric pressure runs (P = 102 kPa A), the apparatus differed from FIG. 1 in that flow controllers 5, 8 and 11 and vacuum pump 9 were located downstream of converter 12, so that it operated at atmospheric pressure.

The conversion under each condition is reported as a fraction of the maximum indicated "$NO_x$" measured for that gas mixture using wet chemical methods or another converter. The efficiency of the system was also tested by using NO as an internal standard. If the indicated $NH_3$/NO ratio remained constant with dilution or upon the addition of a suspected poison, the conversion can be reasonably believed to be quantitative.

TABLE I

| | | | Performance of Platinum-Based Catalytic Converter | | | | |
|---|---|---|---|---|---|---|---|
| T/K | P/kPaA | $X_{O_2}$ | $X_{NH_3}$/ppm | $X_{NO}$/ppm | Special | Balance | Conversion |
| 1030 | 102 | .02 | 400 | 220 | —[c] | He | .98 |
| 1030 | 102 | .17 | 40 | 22 | —[e,f] | $N_2$ | .66 |
| 1030 | 102 | .02 | 400 | 220 | —[g] | He | .89 |

TABLE I-continued

Performance of Platinum-Based Catalytic Converter

| T/K | P/kPaA | $X_{O_2}$ | $X_{NH_3}$/ppm | $X_{NO}$/ppm | Special | Balance | Conversion |
|---|---|---|---|---|---|---|---|
| 1030 | 102 | .04 | 900 | — | —$^{d,f}$ | $N_2$ | .70 |
| 1200 | 102 | .02 | 400 | 220 | —$^{c,g}$ | He | .50 |
| 1030 | 102 | .02 | 400 | 220 | —$^{c,g}$ | He | .96 |
| 1030 | 102 | .04 | 900 | — | —$^d$ | He | 1.01 |
| 1030 | 102 | .02 | 300 | 470 | —$^d$ | He | .98 |
| 1030 | 102 | .01 | 1350 | 1750 | .1 $CO_2$,$^c$ | He | 1.02 |
| 1030 | 102 | .02 | 2650 | 750 | .1 $CO_2$,$^c$ | He | .97 |
| 1030 | 10 | .04 | 385 | 225 | .2 $CO_2$, .1 $H_2O$,$^{c,h}$ | $N_2$ | .98 |
| 1030 | 10 | .04 | 385 | 225 | .1 $H_2O$,$^{c,h}$ | He | .99 |
| 1030 | 10 | .18 | 77 | 45 | —$^{e,h}$ | $N_2$ | .98 |

Notes:
$^a$Due to variations in standard gases available from our suppliers, and to discrepancies between measurements and calculations based on rotameter calibrations, conversion efficiency was reported relative to the most reliable standards. These were indicated for each case.
$^b$Background measurement indicated that there was less than .02 ppm of $N_2$ converted to NO in the converter, even in the presence of 1% $CH_4$ or CO. Similarly, the addition of 1% CO did not reduce the indicated "$NO_x$" level. The background "$NO_x$" (.75 ppm) observed in $O_2$/He mixtures is reasonably believed to be due to slow outgassing of the plumbing.
$^c$Dilution calculations based on Fisher-Porter rotameter sizing procedures.
$^d$Gas titration of .1 N HCl to a Methyl Purple end point.
$^e$This experiment consisted of diluting the previous gas mixture with air. NO served as an internal standard for conversion efficiency.
$^f$This drop in efficiency with sample dilution is quite unexpected and is believed to indicate poisoning by $N_2$, the only major new component in the system. Indeed, the use of $N_2$ as a diluent produced the same effect.
$^g$The converter did not recover its efficiency on removing the air diluent. It was necessary to heat the catalyst to 1300° K. to restore its activity.
$^h$This set of experiments at low-pressure corresponded to the conditions that resulted in poisoning at atmospheric-pressure.

The data in Table I determined four important points. First, it was confirmed that $N_2$ was not converted to NO under the conditions. Second, it was found that the initial presence of NO in the gas mixture did not affect the conversion of $NH_3$. Third, it was found that the conversion efficiency was not affected by the choices of carrier gas, with the notable exception of $N_2$, which rapidly deactivated the catalyst at atmospheric pressure. Fourth, low pressure operation eliminated this problem and the converter could be operated at low pressure for weeks with less than 1% degradation in performance.

EXAMPLE 2

Figure 3:
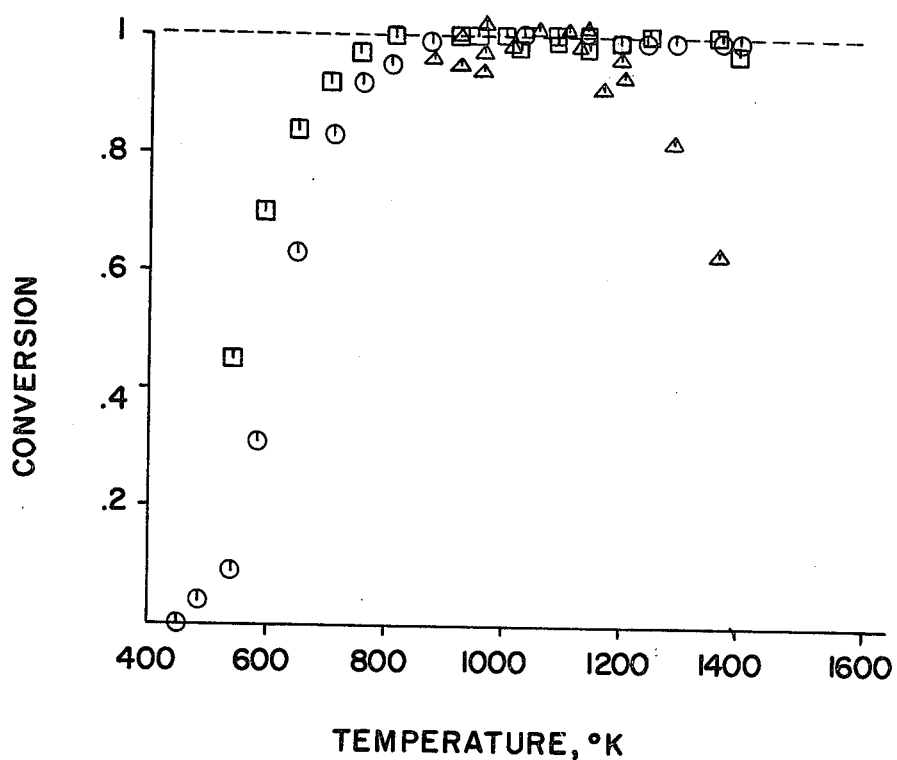
FIG. 3 is a plot of catalyst temperature (°K.) vs. obtained conversion of fixed nitrogen species (expressed as a decimal), illustrating conversion efficiency as a function of temperature for the subject process.

Utilizing the apparatus and general procedure described in Example 1, a series of runs were run to demonstrate the effect of catalyst temperature on the % $NH_3$ conversion at both atmospheric and reduced pressures and % HCN conversion at reduced pressure. The results are illustrated in FIG. 3.

As is seen, the desired reactions clearly dominate the system for both $NH_3$ and HCN conversion from 800°–1100° K. The upper limit for the conversion of $NH_3$ to NO at atmospheric pressure is probably due to non-catalytic conversion of $NH_3$ to $N_2$ above 1200° K. in the inlet/preheater region of the reactor.

EXAMPLE 3

Utilizing the apparatus described in Example 1, low pressure conversion of two separate gas mixtures was carried out over a wide range of concentrations.

Figure 4:
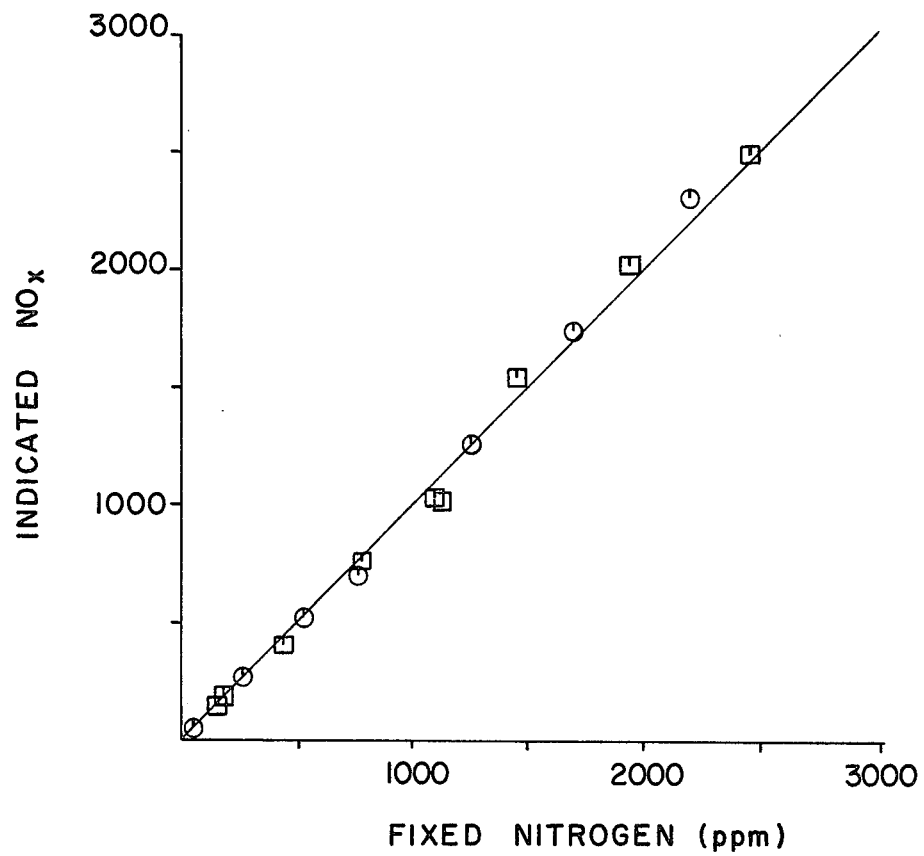
FIG. 4 is a plot of measurement of $NH_3$ and HCN by wet chemical methods ("Fixed Nitrogen") as compared to the same determination by the subject process (Indicated "$NO_x$"). The plot is a least squares fit to the data where.

The results are shown in FIG. 4. The data showed no significant change in conversion efficiency over a range of two orders of magnitude in fixed-nitrogen concentration, giving values of 1.00±0.02 for $NH_3$ and 1.01±0.03 for NCN. This indicates a rapid, accurate and reproducible technique for the measurement of $NH_3$ or HCN in gaseous mixtures.

COMPARATIVE EXAMPLE 1

Utilizing the apparatus described in Example 1, a series of runs was made to illustrate the effect of reduced pressure on the poisoning of the platinum catalyst by $N_2$. First, a standard mixture of 550 ppm $NH_3$, 250 ppm NO, 10% $O_2$, balance He was prepared and analyzed using the catalytic converter at atmospheric pressure to convert the $NH_3$ to NO for analysis. The indicated composition was the same as that calculated for the mixture. This mixture was then diluted fivefold with air, $N_2$, and He to produce three new mixtures, which were, in turn, analyzed, first by the same procedure, then by using the same catalytic converter at reduced pressure. In all cases, the indicated NO concentration was that calculated for the diluted mixture, but the indicated $NH_3$ concentration was only 60-80% of the calculated value if the diluent was air or $N_2$ and the converter was operated at atmospheric pressure. By operating the catalytic converter at reduced pressure, satisfactory values (±2%) of the $NH_3$ concentration were indicated for all of the mixtures.

This result clearly shows the benefit to be realized in improved $NH_3$ measurement accuracy by virtue of improved conversion efficiency, by operating the catalytic converter at reduced pressure.

COMPARATIVE EXAMPLE 2

Utilizing the apparatus and general procedure described in Example 1, a series of runs was made to show the influence of stainless steel and quartz on the accuracy of the $NH_3$ conversion. A gaseous mixture of 15 ppm $NH_3$, 15 ppm NO, 4% $O_2$, balance He was prepared and analyzed using the catalytic converter at atmospheric pressure to convert $NH_3$ to NO for analysis. The indicated composition was the same as that calculated for the mixture. An identical mixture was then prepared and analyzed in a similar apparatus, with a stainless steel tube to serve as both the heater and catalytic converter. The indicated NO concentration was the same as that previously measured, but the indicated $NH_3$ concentration was only 75% of the calculated value, demonstrating the $NH_3$ conversion to NO in the stainless steel converter was incomplete.

This result shows clearly that the stainless steel converter is inferior to the platinum/quartz converter proposed herein for the conversion of $NH_3$ to NO. It is reasonably believed that this inferiority is attributable to the stainless steel vessel, and not to the absence of a platinum catalyst.

COMPARATIVE EXAMPLE 3

Utilizing a modified form of apparatus and general procedure described in Example 1, a series of runs was made to determine the effect of preheat in the process. The modified apparatus consisted of a catalytic converter in which a spiral of platinum wire in a quartz tube served to self-heat and to raise the gaseous mixture to reaction temperature. In the design, the inlet end of the catalyst was inherently close to ambient temperature such that the gaseous mixture entering the catalytic zone was essentially at ambient temperature prior to conversion, and the gas only reached 1100°–1300° K. in the latter part of the reactor.

As previously, the runs consisted of analyzing a gaseous mixture of known composition. A gaseous mixture of 3340 ppm $NH_3$, 1930 ppm NO, 1.3% $O_2$, 8.3% $CO_2$, balance He was prepared and analyzed at atmospheric pressure using the catalytic converter and apparatus described in Example 1. This same mixture was also analyzed using the catalytic converter with the platinum wire heater that also served as the catalyst. The indicated $NH_3$ concentration based on the conversion of $NH_3$ to NO by this converter was only 50% of the calculated value.

This result showed clearly that contacting of the catalyst by the gaseous mixture at less than the desired conversion temperature leads to incomplete conversion of the $NH_3$ to NO. It is reasonably believed that this problem can best be avoided by preheating the gaseous mixture in an inert vessel before contacting the catalyst.

What is claimed is:

1. An improved process for measuring the total concentration of fixed nitrogen species, including NO, $NO_2$, $NH_3$ and HCN, in a gaseous mixture involving the steps of contacting said gaseous mixture with a conversion catalyst at elevated temperature and in the presence of excess elemental oxygen and thereby converting said fixed nitrogen species to NO and measuring the resulting NO concentration and calculating therefrom said total concentration of gaseous fixed nitrogen species, in which the improvement comprises the combined steps of:
   (a) reducing the pressure of said gaseous mixture to about 0.03 MPa or below;
   (b) preheating said gaseous mixture from step (a) to a temperature in the range of about 700°–1100° K in a non-catalytic preheat zone; and
   (c) contacting said preheated gaseous mixture from step (b) with said conversion catalyst at a temperature in the range of about 800°–1100° K. for a sufficient time to convert substantially all of said gaseous fixed nitrogen species to NO.

2. The improved process according to claim 1 wherein said temperature in step (b) is about 800°–1000° K.

3. The improved process according to claim 1 wherein said temperature in step (c) is about 800°–1000° K.

4. The improved process according to claim 1 wherein said temperature in step (b) is substantially the same as said temperature in step (c).

5. The improved process according to claim 1 wherein said non-catalytic preheat zone in step (b) is a fused quartz vessel.

6. The improved process according to claim 1 wherein said pressure in step (a) is about 0.001–0.03 MPa.

7. The improved process according to claim 6 wherein said pressure in step (a) is about 0.005 MPa.

8. The improved process according to claim 1 wherein said conversion catalyst comprises platinum metal.

9. The improved process according to claim 8 wherein said platinum metal is in the form of about 1–200 mesh gauze.

10. An improved process for measuring the total concentration of fixed nitrogen species, including NO, $NO_2$, $NH_3$ and HCN, involving the steps of contacting a gaseous mixture, containing one or more of said species with a conversion catalyst at elevated temperature and in the presence of excess elemental oxygen and thereby converting said fixed nitrogen species to NO and measuring the resulting NO concentration by NO chemiluminescence and calculating therefrom said total concentration of gaseous fixed nitrogen species, in which the improvement comprises the combined steps of:
   (a) reducing the pressure of said gaseous mixture to about 0.001 to 0.030 MPa;
   (b) preheating said gaseous mixture from step (a) to a temperature in the range of about 800°–1000° K in a fused quartz vessel; and
   (c) contacting said preheated gaseous mixture from step (b) with platinum gauze at a temperature in the range of about 800°–1000° K for a sufficient time to convert substantially all of said gaseous fixed nitrogen species to NO.

11. An improved apparatus for measuring the total concentration of fixed nitrogen species in a gaseous mixture, including NO, $NO_2$, $NH_3$ and HCN, involving a means for introducing said gaseous mixture into said apparatus, a catalytic converter for converting said fixed nitrogen species in said gaseous mixture at elevated temperature to NO and an NO detector for measuring the resulting NO concentration in which the improvement comprises the combined elements of:
   (a) means for reducing the pressure of said introduced gaseous mixture to about 0.03 MPa and below; and
   (b) a non-catalytic preheater for preheating said reduced pressure gaseouse mixture in the temperature range of about 700°–1100° K, prior to contacting said catalytic converter.

12. The improved apparatus according to claim 11 wherein said catalytic converter and said preheater comprise one assembly.

13. The improved apparatus according to claim 11 wherein said non-catalytic preheater comprises a quartz vessel in contact with a heating means.

14. The improved apparatus according to claim 13 wherein said quartz is fused quartz.

15. The improved apparatus according to claim 13 wherein said quartz vessel is a U-tube equipped with a gas inlet and outlet.

16. The improved apparatus according to claim 11 wherein said catalytic converter comprises a platinum catalyst in contact with a heating means.

17. The improved apparatus of claim 16 wherein said platinum catalyst is metallic platinum or a platinum alloy stable at elevated temperatures in the presence of elemental oxygen.

18. The improved apparatus of claim 16 wherein said platinum catalyst is platinum gauze of about 50 mesh size.

19. The improved apparatus according to claim 18 wherein said catalytic converter and said preheater are contained in series in a quartz vessel.

20. An improved apparatus for measuring the total concentration of fixed nitrogen species in a gaseous mixture, including NO, $NO_2$, $NH_3$ and HCN, involving a means for introducing said gaseous mixture into said apparatus, a platinum gauze catalytic converter for converting said fixed nitrogen species in said gaseous mixture at elevated temperature to NO and an NO chemiluminescence detector for measuring the resulting NO concentration, in which the improvement comprises the combined elements of:

(a) vacuum means for reducing the pressure of said introduced gaseous mixture to about 0.03 MPa and below; and (b) a quartz preheater for preheating said reduced pressure gaseous mixture in the temperature range of about 700°–1100° K prior to contacting said platinum gauze catalytic converter.

* * * * *